(12) United States Patent
Rhoades

(10) Patent No.: US 7,572,238 B2
(45) Date of Patent: Aug. 11, 2009

(54) HANDHELD SONIC MICRODERMABRASION POROUS APPLICATOR

(75) Inventor: Dean L. Rhoades, Los Angeles, CA (US)

(73) Assignee: DermaNew, Inc., Beverly Hills, CA (US)

( * ) Notice: Subject to any disclaimer, the term of this patent is extended or adjusted under 35 U.S.C. 154(b) by 1208 days.

(21) Appl. No.: 10/349,156

(22) Filed: Jan. 21, 2003

(65) Prior Publication Data
US 2003/0165550 A1    Sep. 4, 2003

Related U.S. Application Data

(63) Continuation-in-part of application No. 09/802,425, filed on Mar. 9, 2001, which is a continuation-in-part of application No. 09/411,712, filed on Oct. 4, 1999, now Pat. No. 6,652,888.

(51) Int. Cl.
*A61H 23/02* (2006.01)
*A61H 7/00* (2006.01)
(52) U.S. Cl. .......................... 601/73; 601/138
(58) Field of Classification Search .......... 601/15, 601/17, 18, 46, 70, 72, 73, 80, 136, 137, 601/138
See application file for complete search history.

(56) References Cited

U.S. PATENT DOCUMENTS

| | | | | |
|---|---|---|---|---|
| 1,653,901 | A | * | 12/1927 | Haessly ........................ 604/23 |
| 1,714,693 | A | * | 5/1929 | Renwick ..................... 607/109 |
| RE19,043 | E | * | 1/1934 | Grison ......................... 601/18 |
| 2,985,166 | A | * | 5/1961 | Burkardt ...................... 601/18 |
| 3,092,111 | A | | 6/1963 | Saperstein |
| 3,852,417 | A | | 12/1974 | McLaughlin |
| 4,102,334 | A | * | 7/1978 | Muchisky .................... 601/73 |
| 4,284,533 | A | | 8/1981 | Imamura et al. |
| 4,344,930 | A | | 8/1982 | MacRae et al. |
| 4,404,965 | A | | 9/1983 | Waits et al. |
| 4,427,001 | A | * | 1/1984 | Kiefer et al. .................. 601/17 |
| 4,887,594 | A | | 12/1989 | Siegel |
| 4,925,327 | A | | 5/1990 | Wirt |
| 4,957,747 | A | | 9/1990 | Stiefel |

(Continued)

FOREIGN PATENT DOCUMENTS

DE    27 18 158 A    11/1978

(Continued)

OTHER PUBLICATIONS www.foamex.com/ftpWs/pdf/Polyurethane Foam The Cinderella Story.pdf, p. 6.*

(Continued)

*Primary Examiner*—Danton DeMille
(74) *Attorney, Agent, or Firm*—Blakely, Sokoloff, Taylor & Zafman, LLP

(57) ABSTRACT

A composition including a base and a plurality of abrasive particles. An apparatus including a head, and an applicator coupled to the head, the applicator having dimensions suitable for contacting localized areas of human skin. A method including applying a composition to an area of human skin, the composition comprising a base and a plurality of abrasive particles, and manipulating the composition over the area of human skin with a handle-operated instrument.

1 Claim, 6 Drawing Sheets

U.S. PATENT DOCUMENTS

| | | | |
|---|---|---|---|
| 4,992,476 A | | 2/1991 | Geria |
| 5,219,571 A | | 6/1993 | Wise |
| 5,360,824 A | | 11/1994 | Barker |
| 5,560,068 A | | 10/1996 | Blake |
| 5,607,980 A | | 3/1997 | McAtee et al. |
| 5,673,455 A | | 10/1997 | Per-Lee et al. |
| 5,679,877 A | | 10/1997 | Erilli et al. |
| 5,753,245 A | | 5/1998 | Fowler et al. |
| 5,756,081 A | | 5/1998 | Wdowik |
| 5,800,446 A | | 9/1998 | Banuchi |
| 5,891,449 A | | 4/1999 | Daniel et al. |
| 6,006,761 A | * | 12/1999 | Meledandri ............... 132/320 |
| 6,010,268 A | * | 1/2000 | Sereg et al. ............... 401/207 |
| 6,090,085 A | | 7/2000 | Mehl, Sr. et al. |
| 6,139,553 A | | 10/2000 | Dotan |
| 6,170,108 B1 | * | 1/2001 | Knight ........................ 15/29 |
| 6,290,976 B1 | | 9/2001 | Messenger |
| 6,294,179 B1 | | 9/2001 | Lee et al. |
| 6,312,397 B1 | * | 11/2001 | Gebhard ..................... 601/15 |
| 6,443,915 B1 | * | 9/2002 | Hwang ....................... 601/15 |
| 6,461,599 B1 | | 10/2002 | Ruben |
| 2001/0018061 A1 | | 8/2001 | Rhoades |
| 2002/0090385 A1 | | 7/2002 | Fox et al. |
| 2002/0156402 A1 | | 10/2002 | Woog et al. |
| 2003/0163068 A1 | * | 8/2003 | Kang .......................... 601/15 |
| 2004/0010222 A1 | * | 1/2004 | Nunomura et al. ......... 604/22 |
| 2004/0171970 A1 | * | 9/2004 | Schleuniger et al. ........ 601/2 |

FOREIGN PATENT DOCUMENTS

| | | | |
|---|---|---|---|
| EP | 0 336 900 A | | 10/1989 |
| EP | 0 571 193 A | | 11/1993 |
| FR | 2 564 318 A | | 11/1985 |
| GB | 1 021 276 A | | 3/1966 |
| WO | WO 92 21306 A | | 12/1992 |
| WO | WO 97/22325 | * | 6/1997 |
| WO | WO 99/21532 | | 5/1999 |

OTHER PUBLICATIONS www.ergaerospace.com/foamproperties/introduction.htm, p. 2.*
Epoxy, Epoxy Definitions (2002), www.primeresins.com/onlineresources/epoxy_definitions.php., 3 pgs.
Chigarina K.M., "Cream Scrub", RU2180214, Mar. 10, 2002, 9 pgs.
Cheski, Peter J., et al., "Method and Apparatus for Microdermabrasion", WO01/95816, Dec. 20, 2001, 12 pgs.
Mehl, Thomas L., et al., "Hand-Held, Multi-Purpose Portable Steamer", WO94/04116, Mar. 3, 1994, 69 pgs.
Merriam-Webster, Merriam-Webster's Collegiate Dictionary (10th Ed. 1998), pp. 272, 749.
Rhoades, Dean, Non-Final OA dated Feb. 26, 2002, U.S. Appl. No. 09/802,425, filed Mar. 9, 2001, 8 pgs.
Rhoades, Dean, Non-Final Office Action dated Feb. 12, 2003, U.S. Appl. No. 09/802,425, filed Mar. 9, 2001, 9 pgs.
Rhoades, Dean, Final Office Action dated Jul. 29, 2003, U.S. Appl. No. 09/802,425, filed Mar. 9, 2001, 11 pgs.
Rhoades, Dean, Non-Final Office Action dated Mar. 11, 2004, U.S. Appl. No. 09/802,425, filed Mar. 9, 2001, 15 pgs.
Rhoades, Dean, Final Office Action dated Dec. 10, 2004, U.S. Appl. No. 09/802,425, filed Mar. 9, 2001, 19 pgs.
The American Heritage Dictionary, The American Heritage Dictionary of the English Language (4th Ed. 2000) [online], "moisturizer" [retrieved on Jul. 22, 2003]; retrieved from the internet <URL:http://www.bartleby.com/61/4/M0370450.html>.

* cited by examiner

HANDHELD SONIC MICRODERMABRASION POROUS APPLICATOR

CROSS-REFERENCE TO RELATED APPLICATIONS

This application is a Continuation-In-Part of application Ser. No. 09/802,425, filed on Mar. 9, 2001, which is a Continuation-In-Part of application Ser. No. 09/411,712, filed on Oct. 4, 1999 now U.S. Pat. No. 6,652,888.

FIELD

The embodiments disclosed herein relate generally to skin treatment.

BACKGROUND

Facial skin rejuvenation has been accomplished by chemical treatment referred to as "chemical peels" or laser treatment referred to as "laser surgery" and exfoliation by machine driven means, such as with emery paper. Such methods generally require medical supervision and involve some risk of deleterious side effects as well as pain and discomfort during treatment. These methods all require long recovery time between treatments.

Microdermabrasion (e.g., microexfoliation, particle skin resurfacing) is a technique in skin care in which a controlled exfoliation of the skin is performed to improve and remove skin abnormalities. A typical microdermabrasion machine consists of a vacuum pump compressor that draws crystals of corundum (aluminum oxide or alumina) from a container through an output tube into a hand piece. When the hand piece is applied to skin it creates a path wherein crystals are drawn across the skin into an suction tube that leads to a disposal container for the used crystals and abraded skin. A filter in the suction tube protects moving parts of the vacuum pump. A technician manipulates the hand piece over the skin of the subject to induce exfoliation.

Thus, a compressor, a corundum supply, a vacuum, and a disposal container are required in order for a specialty clinic, with trained technicians, to conduct microdermabrasion on patients. However, such an elaborate, expensive system is not practical for home use.

DESCRIPTION OF THE DRAWINGS

Various embodiments are illustrated by way of example and not by way of limitation in the figures of the accompanying drawings in which like references indicate similar elements. It should be noted that references to "an," "one," "the," "other," "alternative," or "various" embodiments in this disclosure are not necessarily to the same embodiment, and such references mean at least one.

DETAILED DESCRIPTION

Figure 1:
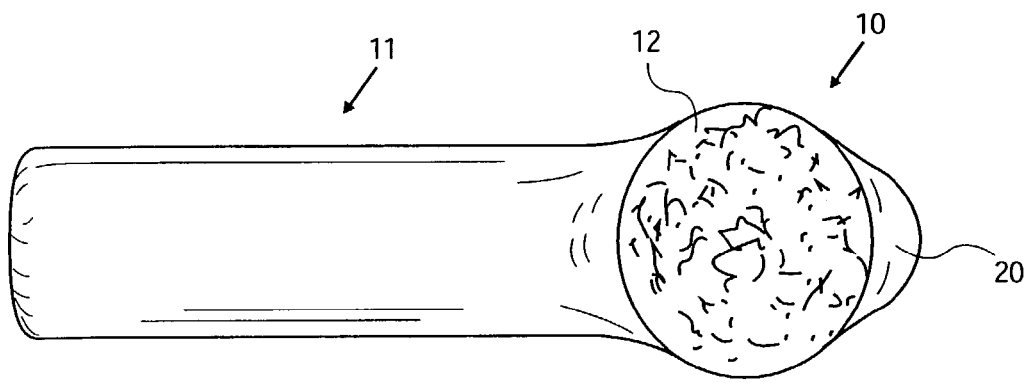
FIG. 1 is a plan view of one embodiment of a portable applicator having a snap-on disk with an applicator pad coupled to a portion of the applicator.

In the following description, for the purposes of explanation, numerous specific details are set forth in order to provide a thorough understanding of the various embodiments. It will be apparent to one skilled in the art that the embodiments may be practiced without some of these specific details. In other instances, certain structures and devices are omitted or simplified in order to avoid obscuring the details of the various embodiments.

The following description and the accompanying drawings provide examples for the purposes of illustration. However, these examples should not be construed in a limiting sense as they are not intended to provide an exhaustive list of all possible implementations.

A composition is disclosed including a base and a plurality of abrasive particles. In one embodiment, the composition includes a base comprising a moisturizer suitable for application to human skin and a plurality of abrasive particles. Suitable abrasive particles include inorganic particles such as corundum (e.g., aluminum oxide, alumina, and $Al_2O_3$), magnesium oxide (e.g., MgO), and precious stones including, but not limited to, diamond, garnet, sapphire, ruby, emerald, and topaz.

In one embodiment, the abrasive particles are microcrystals having an average particle size on the order of 34 microns ($\mu m$) to 556 $\mu m$ (320 to 30 grit). More preferably, the average particle size of the microcrystals is on the order of about 42 $\mu m$ to 198 $\mu m$ (280 to 60 grit).

The abrasive nature of the particles in the composition render the composition suitable as an exfoliator to improve the look and feel of an area of human skin and remove skin abnormalities. More specifically, the abrasive particles tend to remove the outer layer of skin (the epidermis) to expose an underlayer of skin. The human body responds by producing a new layer of skin.

With one or more (and preferably a series) of these exfoliation treatments, it is believed that the skin subject to the treatment may be improved. Such improvements include improvement in the appearance of fine lines, wrinkles, stretch marks, non-inflammatory acne, acne scars, surgical scars, rough or coarse textured skin, age spots, blotchy skin conditions, and sun damaged skin.

In one embodiment, the composition comprises a base that is capable of suspending the plurality of abrasive particles within the base. In various embodiments, a moisturizer is used as a principal component in the base. Moisturizers are believed to reduce water loss from the skin and draw moisture from inner skin layers up into the outer skin layer.

In this regard, the moisturizer can include, in one embodiment, a substance that attracts moisture to the top skin layer (e.g., a humectant). For example, suitable humectants include glycerin, propylene glycol, alpha hydroxy acids, urea, and lactic acid. The moisturizer may also include substances that tend to reduce water loss by creating a barrier. Such substances include, among others, petrolatum, mineral oil, lanolin and silicone derivatives.

Suitable moisturizers may be used in various forms. For example, liquids such as creams, gels, pastes and emollients may be used. In addition to the moisturizer, the base of the composition may further include antioxidants, aromas/fragrances, vitamins (particularly vitamins A, C and E), emulsifiers, toners, acids (e.g., glycolic acid or salicylic acid), scrubs, serums, lotions, liquids, elixirs, sun screens, and tonics. Antimicrobial, bactericidal, and thickening agents may also be included in the composition.

In another embodiment, the base of the composition is a liquid containing a cleansing component including, for example, soaps, salicylic acid, and a lauryl sulfate (e.g. sodium lauryl sulfate or sodium laureth sulfate). The cleansing component base may also be combined with a moisturizer. Other components such as surfactants and emulsifiers may further be included.

In one embodiment, abrasive particles of corundum (e.g., alumina) microcrystals are combined with a cream moisturizer base in an amount of about 5 to 100 grams of corundum per ounce of creme, preferably 10 to 50 grams per ounce, and more preferably 10 to 20 grams per ounce. For example, a suitable composition comprises 20 to 70 percent by weight corundum, 20 to 70 percent aloe gel, and 5 to 20 percent sodium lauryl sulfate.

The abrasive particles suspended in the cream moisturizer provide gentle microdermabrasion of the skin for resurfacing/rejuvenating the skin, leaving it smooth and soft after each treatment without the need of any recovery time. Thus, the treatment may be repeated as often as on a daily basis, in order to reduce and erase fine lines and wrinkles; reduce pore size; reduce or erase sun damage, age spots and skin discoloration; firm skin and muscle tone; reduce sagging; enhance new epidermal cells; and decongest acne skin conditions. This method of rejuvenating the skin, and particularly the facial skin, is ideal for those unwilling or unable to undergo laser surgery, a chemical peel, or machine driven exfoliation.

One example of a suitable composition including corundum (aluminum oxide) microcrystals and a cream moisturizer at approximately 14 grams microcrystals per ounce of cream includes:

| Ingredients | Percentage |
| --- | --- |
| Aluminum Oxide | 35.000 |
| Purified Water | 14.288 |
| Caprylic/Capric Triglyceride | 11.500 |
| Octyl Palmitate | 10.000 |
| Safflower Oil | 10.000 |
| Cetearyl Alcohol | 3.000 |
| Sodium Cetearyl Sulfate | 2.100 |
| Stearic Acid | 5.000 |
| Wheat Germ Oil | 3.000 |
| Propylene Glycol | 2.900 |
| Panthenol | 1.000 |
| Lecethin | 0.500 |
| Cetyl Alcohol | 0.500 |
| Tocopheryl Acetate (vitamin E) | 0.100 |
| Retinyl Palmitate (vitamin A) | 0.100 |
| Ascorbyl Palmitate | 0.100 |
| Extract of Carrot | 0.050 |
| Wheat Germ | 0.050 |
| Wheat Bran | 0.050 |
| Aminomethyl Propanediol | 0.050 |
| Beta Carotene | 0.010 |
| Methylparaben | 0.200 |
| Propylparaben | 0.100 |
| Phenoxyethanol | 0.200 |
| FDC Yellow 5 | 0.001 |
| FDC Yellow 6 | 0.001 |
| Fragrance | 0.200 |

In one embodiment, the composition is provided in a jar (not shown) having a mouth large enough for an applicator of the apparatus described below to be dipped into the composition in the jar. Alternatively, the composition may be scooped out of the jar by hand and applied to the skin area to be treated. Pump mechanisms or squirt bottle tube configurations for dispensing the compositions are also suitable.

One embodiment of a suitable apparatus for buffing the skin includes a portable device having a vibrating head and an applicator coupled to the vibrating head. The applicator has dimensions suitable for contacting localized areas of human skin.

Figure 2:
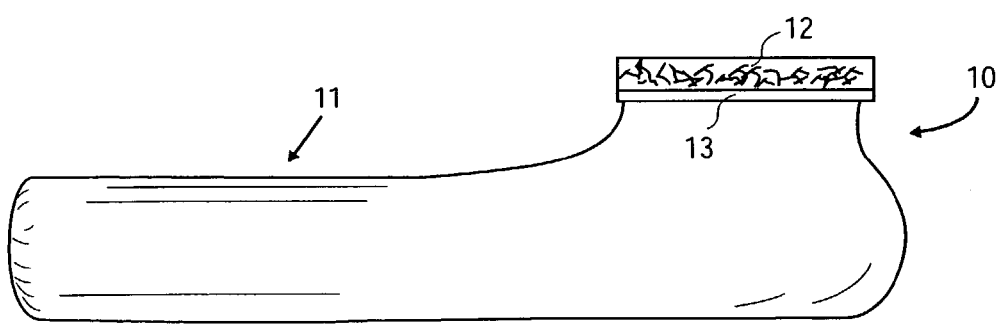
FIG. 2 is a side view of the applicator of FIG. 1.

Referring to FIGS. 1 and 2, a powered (e.g., by a direct current ("DC") battery or by an alternating current ("AC") power source) applicator apparatus (e.g., vibrator) comprises a vibrating device encased in head portion 10 of the apparatus housing. The apparatus also includes handle portion 11, which is adapted to house in an interior volume, a removable/replaceable power source, such as batteries (e.g., multiple AA batteries), optional circuitry for coupling to an AC power source, and circuitry to operate a motor (e.g., DC) driven apparatus. The apparatus, in one embodiment, is formed of a plastic casing.

The apparatus also includes applicator 12 coupled to head portion 10 of the apparatus. In the embodiment shown in FIGS. 1 and 2, applicator 12 is a porous material such as a cloth or sponge having dimensions suitable for contacting an area of human skin, for example, a sponge pad, e.g., a polyurethane sponge pad, a latex sponge pad, or other closed-cell sponge material. One suitable sponge material is commonly referred to as "make-up" sponge material, which is used representatively in the makeup arts. In one embodiment, the pore size of the sponge material ranges from 15 microns to about 410 microns.

Open-cell sponge material may be used either in place of, or in conjunction with, closed-cell material. Likewise, applicator 12 may comprise a non-porous material, such as synthetic rubber, plastic or latex, which can be used in place of, or in conjunction with, porous material.

In one embodiment, the applicator has a pore size that is at least as large as the average particle size of the abrasive particles. In another embodiment, the applicator has a pore size that enables the abrasive particles to move within the applicator during manipulation of the composition over the skin. Pore sizes such as these advantageously allow the abrasive particles to recede into the applicator to prevent the skin from becoming unduly abraded during use. In one embodiment, the pore sizes are sufficiently small that the abrasive particles do not become so deeply-seated in the applicator that the abrasive effects of the particles is lost. Stated differently, the pore size is established such that the level of absorption of the particles allow them to remain effective as an abrasive.

In various embodiments, a heating unit may also be disposed either within applicator 12, adjacent thereto, or both. In an embodiment, the heating unit is capable of heating the applicator to a temperature between 100° F. and 120° F. The heating unit may be, for example, an infrared light, an ultraviolet light, and/or a resistive heating element connected to the power source. The heat from the heating unit advantageously soothes the skin during treatment.

Figure 3:
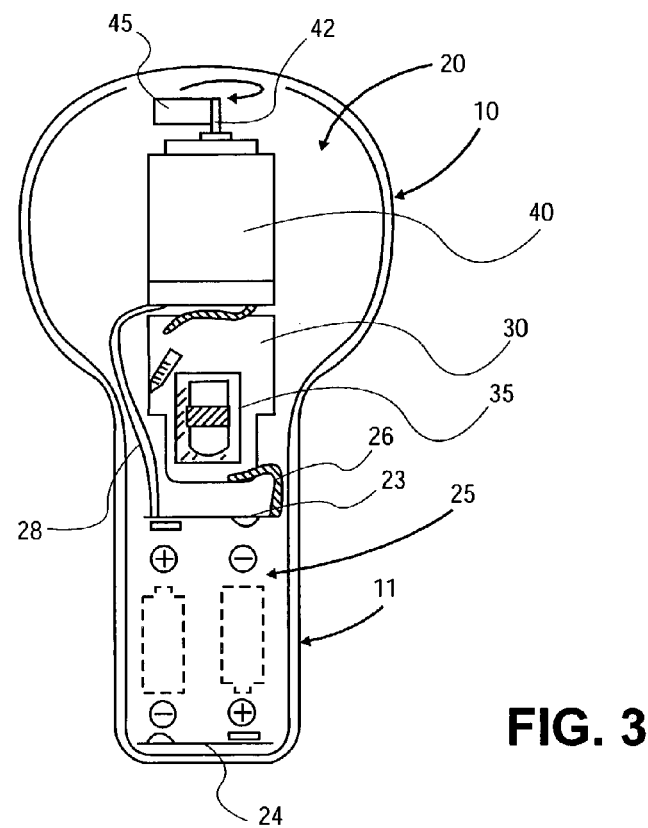
FIG. 3 is a cross-sectional back side view of the applicator of FIG. 1.

FIG. 3 shows a schematic cross-sectional view of the apparatus of FIG. 1, specifically the vibrator portion of the apparatus. In cross-section, the operation of the vibrating mechanism is described. The apparatus includes, in this embodiment, a removable power source. In this case, the apparatus includes handle portion 11 having interior chamber 25 to accommodate the removable power source. In one example, the power source to operate the vibrator is two AA batteries that fit within interior chamber 25 of handle portion 11. Conductors 23 and 24 define ends of the interior chamber. Leads 26 and 28 coupled to conductor 23 bring current to/from motor 40. Lead 26 is coupled to circuit board 30 that includes switch 35 to control the operation of motor 40. Switch 35 may be a two-position switch (ON/OFF) or a multiple position switch for operating motor 40 at multiple speeds.

Motor 40 is disposed in an interior portion 20 of head portion 10 and includes shaft 42 extending from one end of motor 40. Shaft 42 is rotated (as illustrated) with the operation of motor 40.

Coupled to an end of shaft 42 of motor 40 is eccentric mass 45. In this embodiment, eccentric mass 45 is a semi-cylindrical body coupled at its axis to post 42. In this manner, as eccentric mass 45 rotates, its shape generates a rhythmic motion in head portion 10 of the apparatus, which produces a vibration.

Figure 4:
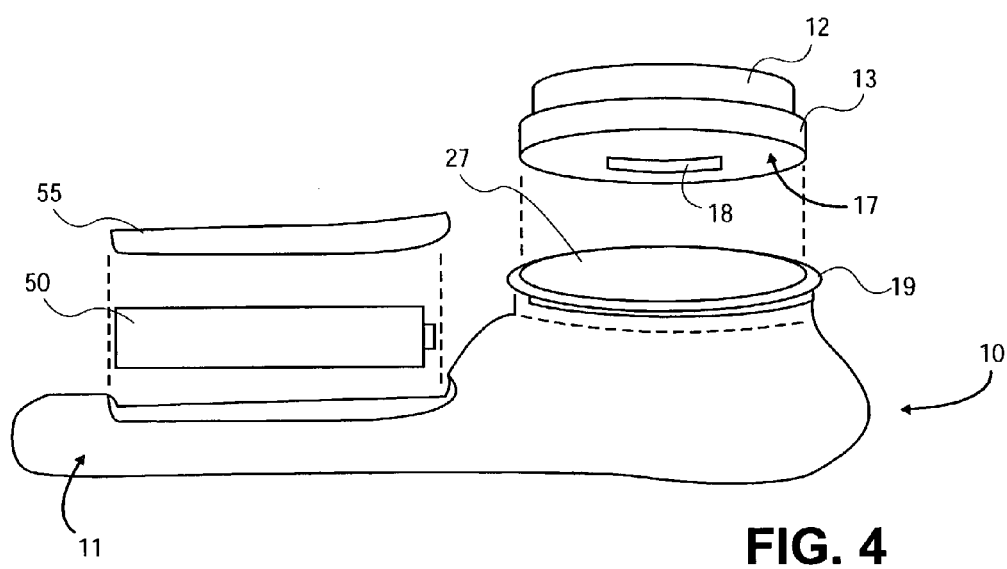
FIG. 4 is an exploded side view of the applicator of FIG. 1.

FIG. 4 shows an exploded side view of the apparatus of FIG. 1. The apparatus includes handle portion 11 that is sized in one portion to be grasped by a human subject. Handle portion 11 includes interior volume 25 for accommodating a removable/replaceable power source, such as one or more batteries 50 (e.g., two AA batteries). Cover 55 snaps into the body of handle portion 11 to enclose the power source within the interior volume of handle portion 11.

FIG. 4 also shows the configuration of applicator 12 relative to head portion 10 of the apparatus. In one embodiment, applicator 12 is coupled to cap 13 (such as by an adhesive between applicator 12 and one surface of cap 13). Cap 13, as illustrated, is a circular body having a diameter similar to the diameter of vibrating head 27 of head portion 10 of the apparatus. In one embodiment, vibrating head 27 has a diameter on the order of about one to two inches (about 2.5-5 centimeters). In one embodiment, the diameter of vibrating head 27 is slightly larger on the order of, for example, 0.01 to 0.03 inches (1-2 millimeters) than the main body of head portion 10 as represented by lip 19.

An underside of cap 13 has interior volume 17. One or more protrusions 18 extend from the side walls of cap 13 (defining interior volume 17) so that cap 13 does not fit easily over lip 19 of head portion 10. Cap 13 is made of a thin plastic material, in one embodiment, which allows the cap to be deformed and snapped over lip 19, vibrating head 27, and onto head portion 10 to securely hold cap 13 in place. Alternatively, the cap may have a groove that snaps over a ridge around the inside wall of the head.

Applicator 12, which is secured to the top of cap 13 may be replaced after many uses. In one embodiment, applicator 12 and cap 13 may be removed from the apparatus after use and cleaned. When it is considered to be no longer useful after, for example, one or more cleanings, applicator 12 (and cap 13) may be discarded and replaced. In one embodiment, applicator 12 can be replaced and discarded after a single use. In this embodiment, applicator 12 may be coupled to the cap 13 by adhesive tape, form fit, or similar manner of removably attaching the applicator 12 to cap 13.

In the embodiment described with reference to FIGS. 1 through 4, an apparatus including a vibrating mechanism is described. It is believed that in applying a composition to an area of human skin and manipulating the composition with a vibrating apparatus (e.g., buffing the skin), as described with reference to FIG. 6 and the accompanying text, the vibrating action of the apparatus (e.g., of the applicator) helps stimulate skin, muscle, and tissue to revitalize the treated area. It is appreciated that, in use, the vibrating mechanism may or may not be used.

It is also contemplated to buff the skin with a mechanism capable of rotating or spinning the applicator either in place of or in conjunction with the vibrating motion described above. In an embodiment, the spinning mechanism is configured to spin the applicator about a central axis of the applicator. In another embodiment, the spinning mechanism is configured to spin the applicator about an off-center axis of the applicator (e.g., to produce a random orbit). A representative random or standard orbit oscillation is on the order of 6,000 or fewer revolutions per minute.

In addition, various embodiments include a sonic wave generator disposed either within the applicator, adjacent thereto, or both. In operation, sonic waves created by the sonic wave generator travel through the applicator and massage the skin of the user. One suitable sonic wave generator is an ultrasound generator that generates sound waves from, for example, a vibrating crystal in a generator. The sound waves may be used to increase circulation to an area being treated.

Figure 5:
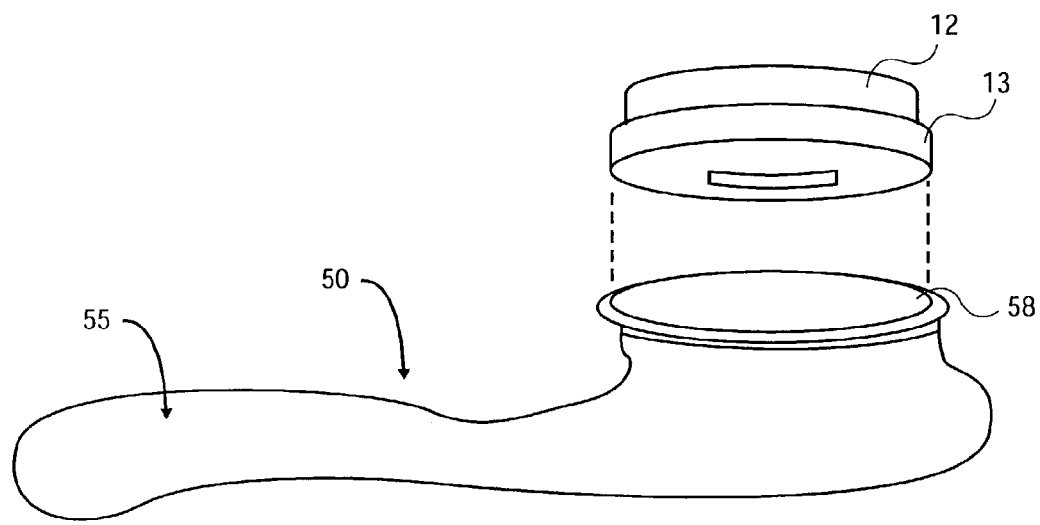
FIG. 5 is an exploded side view of a second embodiment of an applicator.

FIG. 5 shows an embodiment of a manually-manipulated or operated apparatus. Apparatus 50 includes handle 55 suitable for gripping by a hand of a human subject. Handle 55 includes, at one end, head portion 58 having dimensions suitable for accommodating cap 13 and applicator 12 in a manner similar, in one embodiment, to the manner described with reference to FIGS. 1 through 4.

Figure 7:
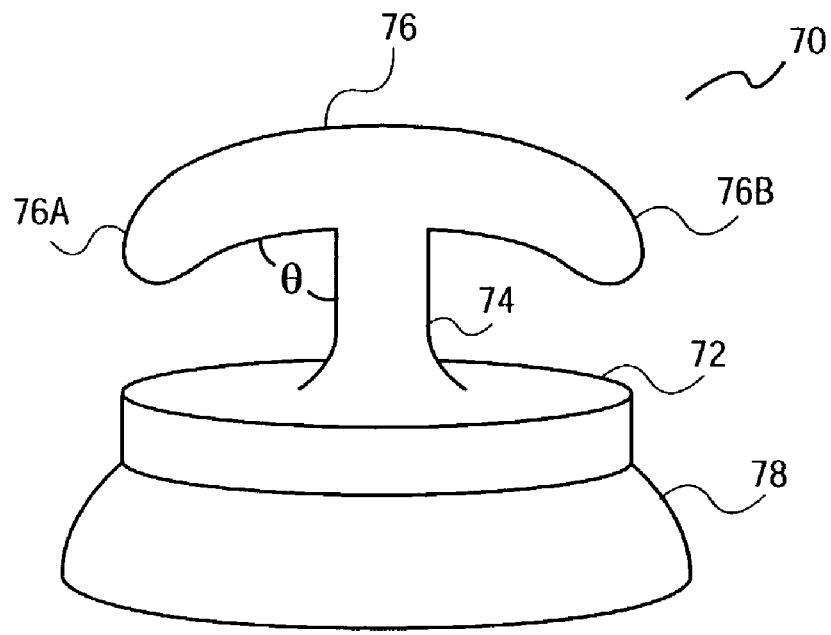
FIG. 7 is a side view of a third embodiment of an applicator.

FIG. 7 shows a further embodiment of a manually-manipulated apparatus. Apparatus 70 includes head portion 72 and a handle portion coupled to the head portion and suitable for gripping by a human hand. The handle portion includes first member 74 extending from head portion 72 and second member 76 coupled to first member 74 at an angle (θ). Angle θ is between 0 and 180 degrees. Second member 76 has first end 76A, second end 76B, and an intermediate portion between first end 76A and second end 76B. Applicator 78 is coupled to head portion 72 and has dimensions suitable for contacting localized areas of human skin.

The shape of the handle portion allows a user to grip the apparatus in different fashions to facilitate application of a suitable composition, as described herein. For example, a user can slide their fingers under second member 76 so that a palm of the user is facing down towards head portion 72. Alternatively, a user can grasp second member 76 with their fingers.

Figure 8:
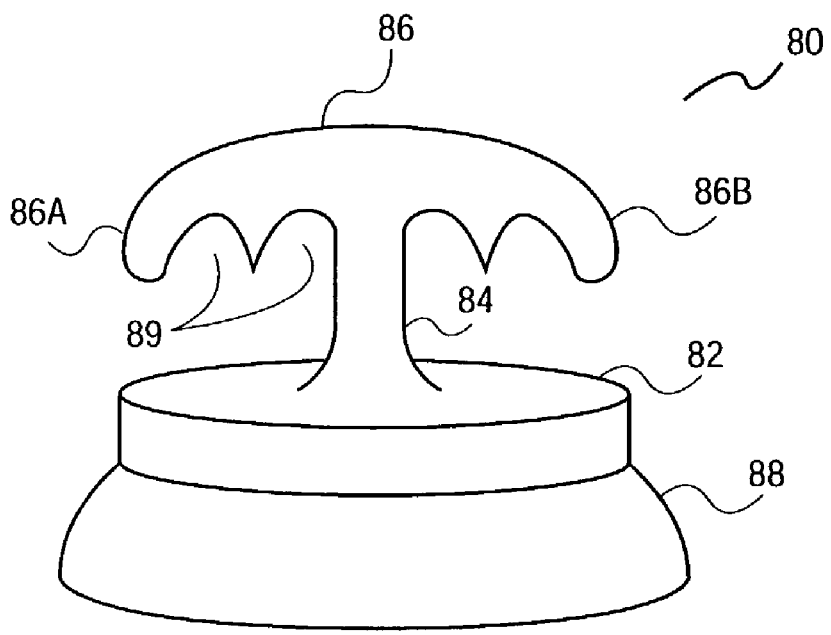
FIG. 8 is a side view of a fourth embodiment of an applicator.

FIG. 8 shows another embodiment of a manually-manipulated apparatus. Apparatus 80 includes head portion 82 and a handle portion coupled to the head portion and suitable for gripping by a human hand. The handle portion includes first member 84 extending from head portion 82 and second member 86 coupled to first member 84. Applicator 88 is coupled to head portion 82 and has dimensions suitable for contacting localized areas of human skin.

Second member 86 has first end 86A, second end 86B, and an intermediate portion between first end 86A and second end 86B. The intermediate portion of second member 86 is coupled to first member 84. In addition, the intermediate portion of second member 86 has grooves 89 formed therein. Each groove 89 can accommodate at least one human finger. Although grooves 89 are disposed on the underside of second member 86 in FIG. 8, grooves 89 may be placed in any orientation and/or location on second member 86 to facilitate handling by a user.

Figure 9:
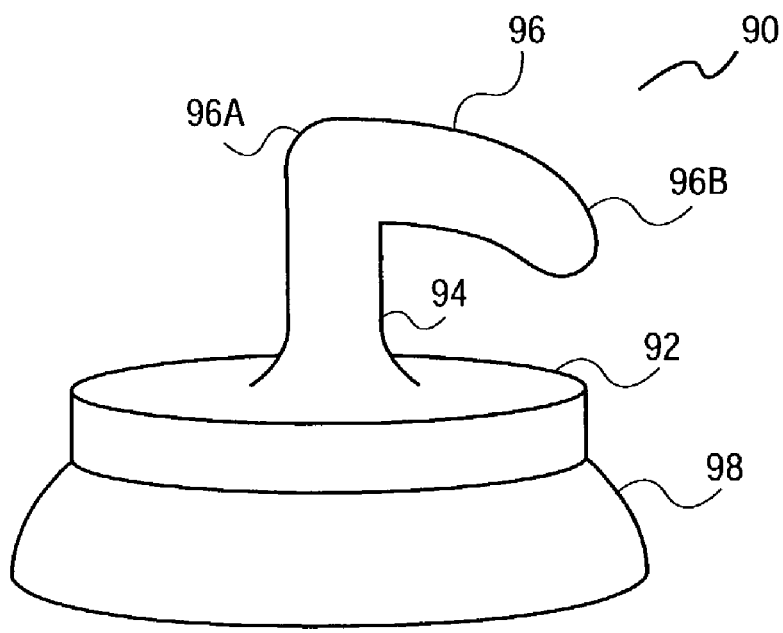
FIG. 9 is a side view of a fifth embodiment of an applicator.

FIG. 9 shows yet another embodiment of a manually-manipulated apparatus. Apparatus 90 includes head portion 92 and a handle portion coupled to the head portion and suitable for gripping by a human hand. The handle portion includes first member 94 extending from head portion 92 and second member 96 coupled to first member 94. Applicator 98 is coupled to head portion 92 and has dimensions suitable for contacting localized areas of human skin.

Second member 96 has first end 96A, second end 96B, and an intermediate portion between first end 96A and second end 96B. First end 96A of second member 96 is coupled to first member 94.

Figure 10:
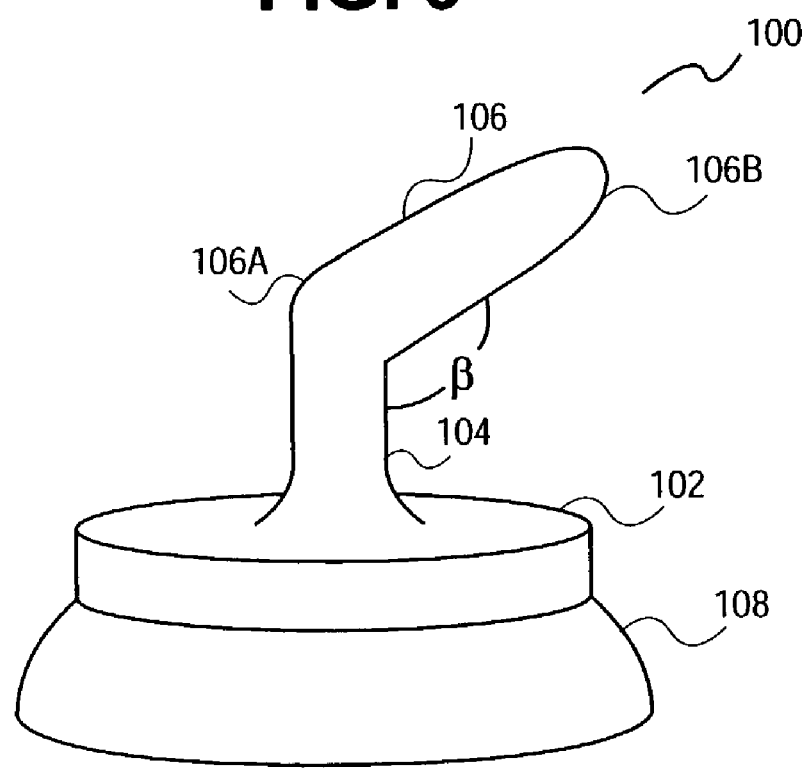
FIG. 10 is a side view of a sixth embodiment of an applicator.

FIG. 10 shows an alternative embodiment of a manually-manipulated apparatus. Apparatus 100 includes head portion 102 and a handle portion coupled to the head portion and suitable for gripping by a human hand. The handle portion includes first member 104 extending from head portion 102 and second member 106 coupled to first member 104. Applicator 108 is coupled to head portion 102 and has dimensions suitable for contacting localized areas of human skin.

Second member 106 has first end 106A, second end 106B, and an intermediate portion between first end 106A and second end 106B. First end 106A of second member 106 is coupled to first member 104 at an angle ($\beta$). In the embodiment shown, $\beta$ is an obtuse angle.

Figure 6:
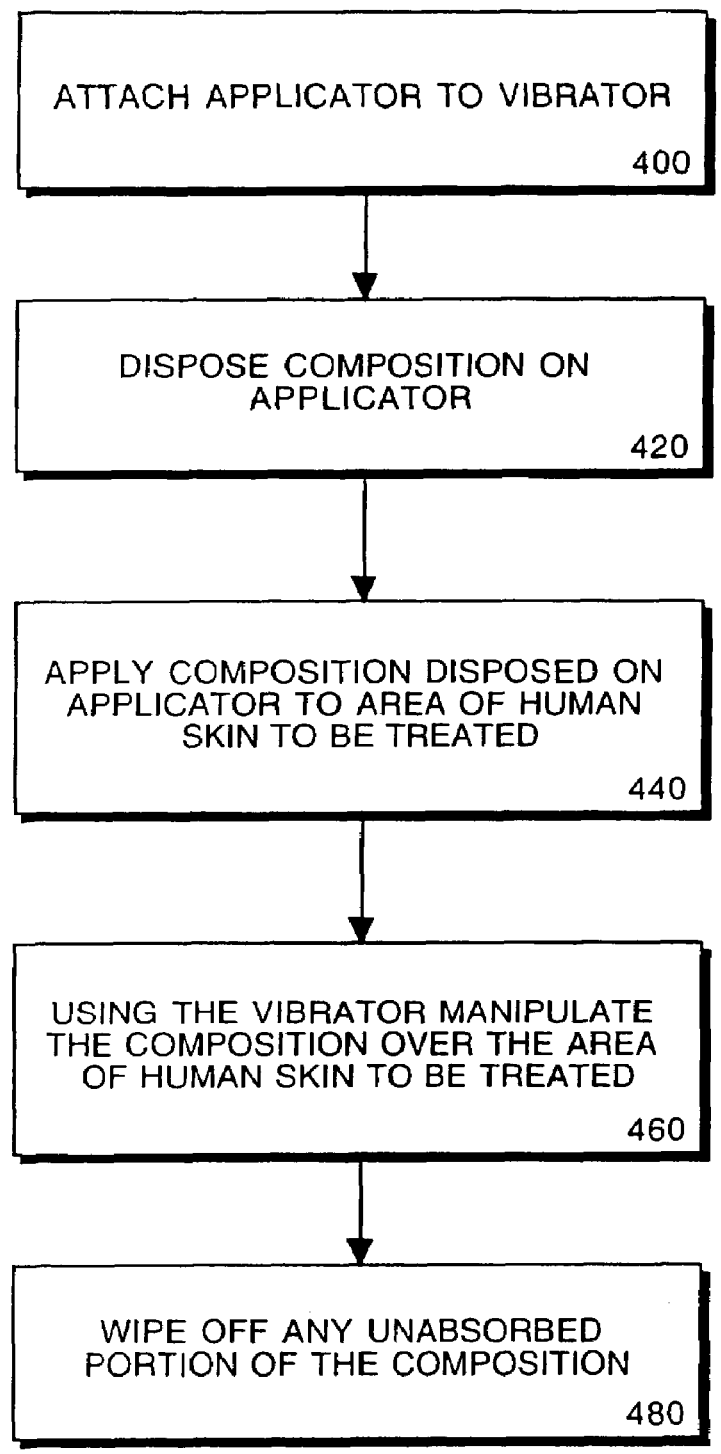
FIG. 6 is a flow chart describing one embodiment of an operation to treat skin.

FIG. 6 shows a flow chart illustrating a method utilizing either the apparatus comprising the motor-driven vibrating mechanism or the manually-manipulated device. Initially, a human user attaches an applicator to the apparatus (e.g., vibrator or random orbit motion apparatus) (block 400). Next, the composition of, for example, moisturizer and abrasive particles, is disposed on the applicator (block 420). This can be accomplished either by dipping the applicator into a container with the composition disposed inside or by disposing the composition directly onto the applicator (i.e., with a dispenser, a squirt bottle tube, spatula or other suitable means).

The user then applies the composition disposed on the applicator to the area of skin to be treated (block 440). One example is applying approximately one-quarter inch of the composition across the entire surface of a porous applicator. The user then dots the area to be treated at locations on the order of, for example, three inches apart.

Subsequently, the user manipulates the composition over the area of skin to be treated with the apparatus (vibrator) (block 460). In an embodiment, manipulation of the composition (block 460) is characterized by moving the apparatus (e.g., vibrator or random orbit motion apparatus) over the area of skin using firm, upward, circular strokes. In one example, the manipulation of the composition is continued for one to ten minutes or until the composition has been worked into the skin and the skin appears soft and smooth.

Finally, the user wipes off any unabsorbed portion of the composition (block 480) and may optionally rinse or cleanse the area. In one embodiment, the composition including a moisturizer as a principal component may be worked in until substantially all of the moisturizer (and any other components) is taken up by the skin and only the abrasive particles remain on the surface of the skin. The abrasive particles may be brushed off and the area of skin cleansed with a mild cleanser. In an alternative embodiment, before applying the composition to the skin, the user cleanses the area of skin with a mild cleanser using gentle circular strokes, rinses the skin with tepid water, and pat the skin dry with a soft towel.

It should be noted that in applying the composition to the skin 440, the user may dab the composition on certain areas of the skin before switching the apparatus (vibrator) on to manipulate the composition over the skin. Alternatively, the user may simultaneously apply the composition to the skin and manipulate the composition over the area of skin to be treated. Alternatively, the user may simultaneously apply the composition to the applicator, dot the area to be treated and manipulate in rotary strokes. Using the vibrator applicator, the user may manipulate the applicator with the vibrator in the on (vibrate) position, or in the off position for a lighter treatment.

It is to be understood that even though numerous characteristics and advantages of various embodiments have been set forth in the foregoing description, together with details of structure, function, and formulations of the various embodiments, this disclosure is illustrative only. Changes may be made in detail, especially matters of structure, management of parts, and compositional formulation, without departing from the scope of the various embodiments as expressed by the broad general meaning of the terms of the appended claims.

What is claimed is:

1. An apparatus comprising:
   a head portion;
   a handle portion coupled to the head portion and suitable for gripping by a human hand, the handle portion comprising a first member extending from the head portion, and a second member coupled to the first member at an angle;
   an applicator comprising a porous mass coupled to the head portion, the porous mass having an average pore size in the range of about 40 microns to about 200 microns and having dimensions suitable for contacting localized areas of human skin; and
   a sonic wave generator to propagate sonic waves through the applicator.

* * * * *